United States Patent

Housley et al.

[11] Patent Number: 5,580,866
[45] Date of Patent: Dec. 3, 1996

[54] THERAPEUTIC 1,4-THIAZEPINES

[75] Inventors: John R. Housley; James E. Jeffery; Kenneth J. Nichol; Bruce J. Sargent, all of Nottingham, England

[73] Assignee: The Boots Company PLC, Notts, United Kingdom

[21] Appl. No.: 424,464

[22] PCT Filed: Nov. 6, 1993

[86] PCT No.: PCT/EP93/03123

§ 371 Date: May 3, 1995

§ 102(e) Date: May 3, 1995

[87] PCT Pub. No.: WO94/11360

PCT Pub. Date: May 26, 1994

[30] Foreign Application Priority Data

Nov. 9, 1992 [GB] United Kingdom ............ 9223441
Nov. 9, 1992 [GB] United Kingdom ............ 9223443

[51] Int. Cl.⁶ ............ A11K 31/55; C07D 281/10
[52] U.S. Cl. ............ 514/211; 540/552
[58] Field of Search ............ 540/552; 512/211

[56] References Cited

U.S. PATENT DOCUMENTS 3,682,962  8/1972  Dickinson ............ 260/327
4,990,707  10/1989  Mais et al. ............ 570/210

FOREIGN PATENT DOCUMENTS 0368063   5/1990   European Pat. Off. .
0565721   10/1993  European Pat. Off. .
4916M     4/1967   France .
92/12148  7/1992   WIPO .
92/21668  12/1992  WIPO .
93/16055  8/1993   WIPO .

OTHER PUBLICATIONS

The international search report.
Boudet et al, C. R. Acad. Sci. Paris Series .C, 282, 249–251 (26 Jan. 1976).
Nair et al, Chem. Abs. 71 (25) 124391p (22 Dec. 1969).
Nair et al, Chem. Abs. 8th Coll. Subj. Index 4452s.
Nair et al, Indian J. Chem. 7 (9) 862–865 (1969).
Szabo et al, Chem. Ber. 119 2904–2913 (1986).
Sternbach et al, J. Org. Chem. 30 (8) 2812–2818 (1965).
Szabo et al, Acta Chimica Hungarica 115 (4) 429–437 (1984).

Primary Examiner—Robert T. Bond
Attorney, Agent, or Firm—Nikaido, Marmelstein, Murray & Oram LLP

[57] ABSTRACT

Compounds of formula I

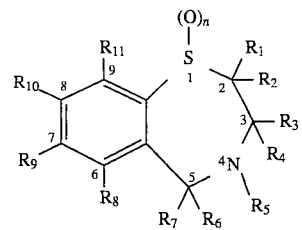

in which n=0, 1 or 2;

$R_1$, $R_2$, $R_6$ and $R_7$ independently represent H or alkyl (optionally substituted by one or more halo);

$R_3$ and $R_4$ independently represent H or alkyl or together represent a group of formula $=NR_{12}$ where $R_{12}$ represents H, hydroxy, alkyl, phenyl or alkoxy; each alkyl, phenyl and alkoxy being optionally substituted with one or more halo;

$R_5$ represents: (a) H, (b) alkyl, (c) a group of formula $-COR_{13}$ in which $R_{13}$ is H, alkyl or phenyl, when $R_3$ and $R_4$ represent H or alkyl (optionally substituted with one or more halo), or (d) a group of formula $-S(O)_pR_{14}$ in which p=1 or 2 and $R_{14}$ is alkyl or phenyl, when $R_3$ and $R_4$ represent H or alkyl (optionally substituted with one or more halo); each alkyl and phenyl optionally substituted with one or more halo;

and $R_8$ to $R_{11}$ independently represent H, halo, cyano, nitro, alkyl alkoxy, alkanoyl, carboxy, alkanoyloxy, carbamoyl (optionally substituted with alkyl or sulphamoyl (optionally substituted with alkyl of 1 to 4 carbon atoms); each alkyl, alkoxy, alkanoyl or alkanoyloxy optionally substituted with one or more halo;

have utility in the treatment of seizures and/or neurological disorders such as epilepsy and/or as neuroprotective agents to protect against conditions such as stroke.

32 Claims, No Drawings

THERAPEUTIC 1,4-THIAZEPINES

This application is a 371 of PCT/EP93/03123 filed Nov. 6, 1993. Priority is also claimed of British applications GB 9223441.8 and GB 9223443.4, both filed 9 Nov. 1992.

This invention relates to derivatives of 2,3,4,5-tetrahydro-1,4-benzothiazepines, to pharmaceutical compositions containing them, to processes for their preparation and to their use in the treatment of seizures and/or neurological disorders such as epilepsy and/or as neuroprotective agents to protect against conditions such as stroke.

In particular the present invention provides compounds of formula I

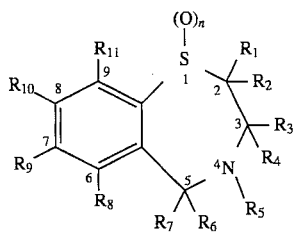

in which:

n=0, 1 or 2

$R_1$, $R_2$, $R_6$ and $R_7$ independently represent H or alkyl of 1 to 4 carbon atoms (optionally substituted with one or more halo);

$R_3$ and $R_4$ independently represent H or alkyl of 1 to 4 carbon atoms; or together represent a group of formula $=NR_{12}$ where $R_{12}$ represents H, hydroxy, alkyl of 1 to 4 carbon atoms, phenyl or alkoxy of 1 to 4 carbon atoms; each alkyl, phenyl and alkoxy being optionally substituted with one or more halo;

$R_5$ represents: (a) H, (b) alkyl of 1 to 4 carbon atoms, (c) a group of formula $-COR_{13}$ in which $R_{13}$ represents H, alkyl of 1 to 4 carbon atoms or phenyl, when $R_3$ and $R_4$ represent H or alkyl (optionally substituted with one or more halo), or (d) a group of formula $-S(O)_pR_{14}$ in which p=1 or 2 and $R_{14}$ is alkyl of 1 to 4 carbon atoms or phenyl, when $R_3$ and $R_4$ represent H or alkyl (optionally substituted with one or more halo); each alkyl and phenyl being optionally substituted with one or more halo;

$R_8$ to $R_{11}$ independently represent H, halo, cyano, nitro, alkyl of 1 to 4 carbon atoms, alkoxy of 1 to 4 carbon atoms, alkanoyl of 1 to 4 carbon atoms, carboxy, alkanoyloxy of 1 to 4 carbon atoms, carbamoyl (optionally substituted with alkyl of 1 to 4 carbon atoms) or sulphamoyl (optionally substituted with alkyl of 1 to 4 carbon atoms); each alkyl, alkoxy, alkanoyl and alkanoyloxy being optionally substituted with one or more halo;

their stereoisomers; and pharmaceutically acceptable salts thereof;

with the provisos that:
(i) when n=0; at least one of $R_1$ to $R_{11}$ is other than H;
(ii) when n=0, 1 or 2; $R_1$, $R_2$ and $R_3$ are independently H or alkyl; $R_4$ and $R_6$ are both H; $R_5$ is H, alkyl or alkanoyl; and one of $R_8$ or $R_9$ and one of $R_9$ to $R_{10}$ are separately H, halo, nitro, alkyl, alkoxy or trifluoromethyl, the remainder of $R_8$ to $R_{11}$ being H; $R_7$ is other than alkyl;

have utility in the treatment of seizures and/or neurological disorders such as epilepsy and/or as neuroprotective agents to protect against conditions such as stroke.

Compounds of formula I where n=0; $R_1$ to $R_4$, $R_6$ to $R_8$ and $R_{11}$ are all H; $R_5$ is H or acetyl; and $R_9$ and $R_{10}$ are both methoxy; are known from Szabo et al, Chem. Ber., 119, pages 2904–2913, (1986).

Compounds of formula I where n=0 or 2; $R_1$ to $R_6$, $R_8$ and $R_{11}$ are all H; $R_7$ is methyl; and $R_9$ and $R_{10}$ are both methoxy; are known from J. Org. Chem., 30 (8), pages 2812–2818, (1965), (Eng).

Compounds of formula I where n=0; $R_1$, $R_2$, $R_5$, $R_6$ and $R_7$ are all H; $R_3$ is a straight chain alkyl of 1 to 4 carbon atoms; $R_4$ is a straight chain alkyl of 2 to 4 carbon atoms; and $R_8$ to $R_{11}$ are independently H, halo, nitro, alkyl of 1 to 4 carbon atoms (optionally substituted by one or more halo) or alkoxy of 1 to 4 carbon atoms (optionally substituted by one or more halo); are known as intermediates in the preparation of the compounds claimed in International patent application WO 93/16055 (Wellcome) (see formula XIV, page 18).

Compounds of formula I where n=0, 1 or 2; $R_1$, $R_2$ and $R_3$ are independently H or alkyl of 1 to 4 carbon atoms; $R_4$ and $R_6$ are both H; $R_5$ is H, alkyl of 1 to 4 carbon atoms or alkanoyl of 1 to 5 carbon atoms; $R_7$ is alkyl of 1 to 4 carbon atoms and one of $R_8$ or $R_9$ and one of $R_{10}$ or $R_{11}$ are independently H, halo, nitro, alkyl of 1 to 4 carbon atoms, alkoxy of 1 to 4 carbon atoms, or trifluoromethyl, the remainder of $R_8$ to $R_{11}$ being H; are known from French patent application 4916-M (Hoffmann la Roche) (corresponding inter alia to AU 409345) and are stated to have pharmaceutical activity as anti-agconvulsants. The application does not contain any pharmaceutical data to support this statement.

Compounds of formula I where n=0; $R_1$ to $R_4$, $R_6$ to $R_8$, $R_{10}$ and $R_{11}$ are all H; $R_5$ is H or bromoacetyl; and $R_9$ is H or alkoxy of 1 to 3 carbon atoms; are known as intermediates in the preparation of compounds claimed in International patent application WO 92/12143 (Kaneko) (see pages 4, 5 and 7) (corresponding to EP 0565721).

Compounds of formula I where n=0 or 1; $R_1$ to $R_4$, $R_6$ and $R_7$ are independently H or alkyl of 1 to 4 carbon atoms; $R_5$ is H, alkyl of 1 to 4 carbon atoms or alkanoyl of 1 to 5 carbon atoms; and one of $R_8$ or $R_9$ and one of $R_9$ or $R_{10}$ are separately H, halo, cyano, nitro, alkyl of 1 to 4 carbon atoms, alkanoyl of 1 to 5 carbon atoms or alkanoyloxy of 1 to 4 carbon atoms the remaining one of $R_8$ or $R_9$ being H or chloro and the remaining one of $R_9$ to $R_{10}$ being H; are known as Freidel Crafts catalysts from European patent application 0368063 (Bayer) (claiming priority from DE 3837574 and DE 3837575 and corresponding to US 4990707).

Compounds of formula I where n=0; $R_1$ to $R_4$ and $R_6$ to $R_{11}$ are all H; and $R_5$ is H or benzoyl; are known from Boudet et al, C. R. Acad. Sci. Paris Series C, 282, pages 249–251 (26 Jan. 1976).

Compounds of formula I where n=0, $R_1$ to $R_3$ and $R_6$ to $R_{11}$ are all H; $R_4$ is H or methyl; and $R_5$ is dichloroacetyl; where n=1 or 2, $R_1$ to $R_3$ and $R_5$ to $R_{11}$ are all H and $R_4$ is H or methyl; and salts of compounds of formula I where n=1 or 2, $R_1$ to $R_{11}$ are all H; and the salt is hydrochloride salt; are known from Indian J. Chem., 7(9), pages 862–5, (Eng) (in conjunction with Chem. Abs., 71, 124391p, (1969) and Chem. Abs. 8th Coll. Subst. Ind., p4452S).

Therefore the present invention provides novel compounds of formula II

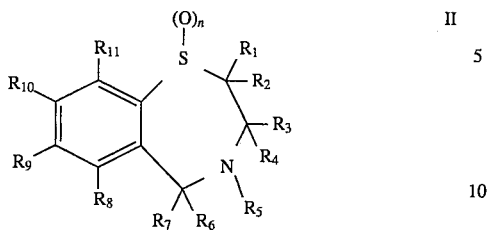

in which:

$n=0$, 1 or 2; $R_1$, $R_2$, $R_6$ and $R_7$ independently represent H or alkyl of 1 to 4 carbon atoms (optionally substituted with one or more halo);

$R_3$ and $R_4$ independently represent H or alkyl of 1 to 4 carbon atoms; or together represent a group of formula $=NR_{12}$ where $R_{12}$ represents H, hydroxy, alkyl of 1 to 4 carbon atoms, phenyl or alkoxy of 1 to 4 carbon atoms; each alkyl, phenyl and alkoxy being optionally substituted with one or more halo;

$R_5$ represents: (a) H, (b) alkyl of to 4 carbon atoms, (c) a group of formula $-COR_{13}$ in which $R_{13}$ represents H, alkyl of 1 to 4 carbon atoms or phenyl, when $R_3$ and $R_4$ represent H or alkyl (optionally substituted by one or more halo), or (d) a group of formula $-S(O)_pR_{14}$ in which $p=1$ or 2 and $R_{14}$ is alkyl of 1 to 4 carbon atoms or phenyl, when $R_3$ and $R_4$ represent H or alkyl (optionally substituted by one or more halo); each alkyl and phenyl being optionally substituted with one or more halo;

$R_8$ to $R_{11}$ independently represent H, halo, cyano, nitro, alkyl of 1 to 4 carbon atoms, alkoxy of 1 to 4 carbon atoms, alkanoyl of 1 to 4 carbon atoms, carboxy, alkanoyloxy of 1 to 4 carbon atoms, carbamoyl (optionally substituted with alkyl of 1 to 4 carbon atoms) or sulphamoyl (optionally substituted with alkyl of 1 to 4 carbon atoms); each alkyl, alkoxy, alkanoyl and alkanoyloxy being optionally substituted with one or more halo;

their stereoisomers; and pharmaceutically acceptable salts thereof;

with the provisos that:

(A) when $n=0$; $R_1$ to $R_4$, $R_6$ to $R_8$ and $R_{11}$ are all H; $R_5$ is H or acetyl; and $R_9$ is methoxy; $R_{10}$ is other than methoxy;

(B) when $n=0$ or 2; $R_1$ to $R_6$, $R_8$ and $R_{11}$ are all H; $R_7$ is methyl; and $R_9$ is methoxy; $R_{10}$ is other than methoxy;

(C) when $n=0$; $R_1$, $R_2$, $R_5$, $R_6$ and $R_7$ are all H; $R_3$ is a straight chain alkyl; and $R_8$ to $R_{11}$ are independently H, halo, nitro, alkyl (optionally substituted with one or more halo) or alkoxy (optionally substituted with one or more halo); $R_4$ is other than a straight chain alkyl of 2 to 4 carbon atoms;

(D) when $n=0$, 1 or 2; $R_1$, $R_2$ and $R_3$ are independently H or alkyl; $R_4$ and $R_6$ are both H; $R_5$ is H, alkyl or alkanoyl; one of $R_8$ or $R_9$ and one of $R_{10}$ to $R_{11}$ are independently H, halo, nitro, alkyl, alkoxy or trifluoromethyl, the remainder of $R_8$ to $R_{11}$ being H; $R_7$ is other than alkyl;

(E) when $n=0$; $R_1$ to $R_4$, $R_6$ to $R_8$ and $R_{10}$ to $R_{11}$ are all H; and $R_5$ is H or bromoacetyl; $R_9$ is other than H or alkoxy of 1 to 3 carbon atoms;

(F) when $n=0$ or 1; $R_1$ to $R_4$, $R_6$ and $R_7$ are independently H or alkyl; and one of $R_8$ or $R_9$ and one of $R_9$ or $R_{10}$ are separately H, halo, cyano, nitro, alkyl, alkoxy, alkanoyl or alkanoyloxy, the remaining one of $R_8$ or $R_9$ being H or chloro and the remaining one of $R_9$ to $R_{10}$ being H; $R_5$ is other than H, alkyl or alkanoyl;

(G) when $n=0$; and $R_1$ to $R_4$ and $R_6$ to $R_{11}$ are all H; $R_5$ is other than H or benzoyl;

(H) when $n=0$; $R_1$ to $R_3$ and $R_6$ to $R_{11}$ are all H; and $R_4$ is H or methyl; $R_5$ is other than dichloroacetyl; when $n=1$ or 2; and $R_1$ to $R_3$ and $R_5$ to $R_{11}$ are all H; $R_4$ is other than H or methyl; and when $n=1$ or 2; and $R_1$ to $R_{11}$ are all H; the salt of compounds of formula I is other than a hydrochloride salt.

Preferred compounds of formula I or II are those in which (with the provisos (i) and (ii) above):

$n=0$ or 1;

$R_1$, $R_2$, $R_6$ and $R_7$ are independently H or methyl;

$R_3$ and $R_4$ are independently H or methyl; or together represent imino, methylimino, phenylimino, hydroxyimino or methoxyimino;

$R_5$ is H or methyl, and when $R_3$ and $R_4$ are H or methyl, $R_5$ is formyl, acetyl, propionyl, benzoyl, methylsulphinyl, methylsulphonyl or ethylsulphonyl; one of $R_8$ to $R_{11}$ is H, fluoro, chloro, bromo, iodo, methyl (optionally substituted with one or more halo), methoxy (optionally substituted by one or more halo), nitro, cyano, carboxy, acetyl, dimethylcarbamoyl or dimethylsulphamoyl; the remainder of $R_8$ to $R_{11}$ being H;

their stereoisomers; and pharmaceutically acceptable salts thereof.

More preferred compounds of formula I or II are those in which (with the provisos (i) and (ii) above):

$n=0$ or 1;

$R_1$, $R_2$, $R_6$ and $R_7$ are H; $R_3$ and $R_4$ are H; or together are methylimino, phenylimino, hydroxyimino or methoxyimino;

$R_5$ is H or methyl, and when $R_3$ and $R_4$ are H, $R_5$ is formyl, acetyl, propionyl, benzoyl, methylsulphinyl, methylsulphonyl or ethylsulphonyl;

$R_8$ is methyl, fluoro or chloro;

$R_9$ to $R_{11}$ are all H;

their stereoisomers; and pharmaceutically acceptable salts thereof.

Specific compounds of formula I or II in which $n=0$ are:

6-chloro-2,3,4,5-tetrahydro-1,4-benzothiazepine;

6-fluoro-2,3,4,5-tetrahydro-1,4-benzothiazepine;

6-methyl-2,3,4,5-tetrahydro-1,4-benzothiazepine;

6-chloro-4-methyl-2,3,4,5-tetrahydro-1,4-benzothiazepine;

4-formyl-2,3,4,5-tetrahydro-1,4-benzothiazepine;

4-acetyl-2,3,4,5-tetrahydro-1,4-benzothiazepine;

4-acetyl-6-chloro-2,3,4,5-tetrahydro-1,4-benzothiazepine;

4-acetyl-6-fluoro-2,3,4,5-tetrahydro-1,4-benzothiazepine;

4-acetyl-6-methyl-2,3,4,5-tetrahydro-1,4-benzothiazepine;

4-propionyl-2,3,4,5-tetrahydro-1,4-benzothiazepine;

6-chloro-4-propionyl-2,3,4,5-tetrahydro-1,4-benzothiazepine;

4-benzoyl-6-chloro-2,3,4,5-tetrahydro-1,4-benzothiazepine;

6-chloro-4-methylsulphinyl-2,3,4,5-tetrahydro-1,4-benzothiazepine;

4-methylsulphonyl-2,3,4,5-tetrahydro-1,4-benzothiazepine;

6-chloro-4-methylsulphonyl-2,3,4,5-tetrahydro-1,4-benzothiazepine;

6-fluoro-4-methylsulphonyl-2,3,4,5-tetrahydro-1,4-benzothiazepine;

6-methyl-4-methylsulphonyl-2,3,4,5-tetrahydro-1,4-benzothiazepine;

4-ethylsulphonyl-2,3,4,5-tetrahydro-1,4-benzothiazepine;

6-chloro-4-ethylsulphonyl-2,3,4,5-tetrahydro-1,4-benzothiazepine;

3-hydroxyimino-2,3,4,5-tetrahydro-1,4-benzothiazepine;

6-chloro-3-hydroxyimino-2,3,4,5-tetrahydro-1,4-benzothiazepine;

3-hydroxyimino-6-methyl-2,3,4,5-tetrahydro-1,4-benzothiazepine;

3-methoxyimino-2,3,4,5-tetrahydro-1,4-benzothiazepine;

6-chloro-3-methoxyimino-2,3,4,5-tetrahydro-1,4-benzothiazepine;

3-methylimino-2,3,4,5-tetrahydro-1,4-benzothiazepine;

6-chloro-3-phenylimino-2,3,4,5-tetrahydro-1,4-benzothiazepine;

their stereoisomers; and pharmaceutically acceptable salts thereof.

Specific compounds of formula I or II in which n=1 are:

6-chloro-2,3,4,5-tetrahydro-1,4-benzothiazepine 1-oxide;

4-acetyl-2,3,4,5-tetrahydro-1,4-benzothiazepine 1-oxide;

4-acetyl-6-chloro-2,3,4,5-tetrahydro-1,4-benzothiazepine 1-oxide;

4-methylsulphonyl-2,3,4,5-tetrahydro-1,4-benzothiazepine 1-oxide;

6-chloro-4-methylsulphonyl-2,3,4,5-tetrahydro-1,4-benzothiazepine 1-oxide;

their stereoisomers; and pharmaceutically acceptable salts thereof.

It will be understood that a group containing a chain of three or more carbon atoms may be straight or branched. The term 'halo' as used herein signifies fluoro, chloro, bromo or iodo.

Certain compounds of formula I or II may form salts with organic or inorganic acids. Reference hereinafter to compounds of formula I or II includes all such salts of compounds of formula I or II which are pharmaceutically acceptable. Particularly suitable salts of compounds of formula I or II include, for example, salts with inorganic acids, for example hydrochlorides, hydrobromides, hydriodides, nitrates, sulphates and phosphates, salts with organic acids, for example maleates, acetates, citrates, fumarates, tartrates, succinates, benzoates, pamoates, palmitates, methylsulphates, dodecanoates and salts with acidic amino acids such as glutamic acid. It will be appreciated that such salts, provided they are pharmaceutically acceptable, may be used in therapy in place of the corresponding compounds of formula I or II. Such salts are prepared by reacting the compound of formula I or II with a suitable acid in a conventional manner.

Certain compounds of formula I or II or their salts may exist in more than one crystal form and the present invention includes each crystal form and mixtures thereof.

Certain compounds of formula I or II or their salts may also exist in the form of solvates, for example hydrates, and the present invention includes each solvate and mixtures thereof.

It will be appreciated by those skilled in the art that certain compounds of formula I or II contain one or more chiral centres. Thus, for example compounds of formula I or II in which n is 1 contain a chiral centre at the sulphur atom; compounds of formula I or II in which $R_1$ and $R_2$ are not identical contain a chiral centre at the 2-carbon atom; compounds of formula I or II in which $R_3$ and $R_4$ are not identical contain a chiral centre at the 3-carbon atom; and compounds of formula I or II in which $R_6$ and $R_7$ are not identical contain a chiral centre at the 5-carbon atom. A compound of formula I or II containing a single chiral centre may exist in two enantiomeric forms. The present invention includes each enantiomer of compounds of formula I or II and mixtures thereof.

The enantiomers may be obtained by methods known to those skilled in the art. Such methods typically include:

resolution via formation of diastereoisomeric salts or complexes which may be separated, for example, by crystallisation;

formation of diastereoisomeric derivatives or complexes which may be separated, for example, by crystallisation, gas-liquid chromatography or liquid chromatography, followed by the liberation of the desired enantiomer from the separated derivative;

selective derivatisation of one enantiomer by reaction with an enantiomer-specific reagent, for example enzymatic esterification, oxidation or reduction, followed by separation of the modified and unmodified enantiomers; or gas-liquid chromatography or liquid chromatography in a chiral environment, for example on a chiral support such as silica with a bound chiral ligand, or in the presence of a chiral solvent.

Alternatively, it may be possible to synthesise a specific enantiomer by asymmetric synthesis using optically active reagents, substrates, catalysts or solvents, or to convert one enantiomer into the other by asymmetric transformation.

When a compound of formula I or II contains more than one chiral centre it may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of formula I or II and mixtures thereof.

It will be appreciated that where the active moiety is transformed by the separation procedures described above, a further step may be required to convert the transformation product back to the active moiety.

Certain compounds of formula I or II may exist in different tautomeric forms or as different geometric isomers, for example when $R_3$ and $R_4$ together represent a group of formula $=NR_{12}$. The present invention includes each tautomer and/or geometric isomer and mixtures thereof.

Certain compounds of formula I or II may exist in zwitterionic form and the present invention includes each zwitterionic form and mixtures thereof.

The present invention also relates to pharmaceutical compositions comprising a therapeutically effective amount of a compound of formula I or II together with a pharmaceutically acceptable diluent or carrier. Such pharmaceutical compositions may be used as neuroprotective agents to protect against conditions such as stroke and/or for the treatment of seizures and/or neurological disorders such as epilepsy. Specific compounds which may be incorporated into the compositions of the present invention are the compounds exemplified herein.

As used hereinafter, the term 'active compound' denotes one or more compound or compounds of formula I or II. In therapeutic use, the active compound may be administered orally, rectally or parenterally, preferably orally. Thus the therapeutic compositions of the present invention may take the form of any of the known pharmaceutical compositions for such methods of administration. The compositions may be formulated in a manner known to those skilled in the art, to give a controlled release, for example rapid release or sustained release, of the active compound. Pharmaceutically acceptable carriers suitable for use in such compositions are well known in the art of pharmacy. The compositions may contain from about 0.1% to about 99% by weight of active compound and are generally prepared in unit dosage form. Preferably the unit dosage of active ingredient is from about 1 mg to about 1000 mg. The excipients used in the preparation of these compositions are the excipients known in the pharmacist's art.

Preferably the compositions of the invention are administered orally in the known pharmaceutical forms for such administration. Dosage forms suitable for oral administration may comprise tablets, pills, capsules, caplets, granules, powders, elixirs, syrups, solutions and aqueous or oil suspensions.

Solid oral dosage forms, for example tablets, may be prepared by mixing the active compound with one or more of the following ingredients:

inert diluents, for example lactose, powdered sugar, pharmaceutical grade starch, kaolin, mannitol, calcium phosphate or calcium sulphate;

disintegrating agents, for example maize starch, methyl cellulose, agar, bentonite, cellulose, wood products, alginic acid, guar gum, citrus pulp, carboxymethylcellulose or sodium lauryl sulphate;

lubricating agents, for example magnesium stearate, boric acid, sodium benzoate, sodium acetate, sodium chloride, leucine or polyethylene glycol;

binders, for example starch, gelatin, sugars (such as sucrose, molasses or lactose), or natural and synthetic gums (such as acacia, sodium alginate, extract of Irish moss, carboxymethylcellulose, methylcellulose, ethylcellulose, polyethylene glycol, waxes, microcrystalline cellulose or polyvinylpyrrolidone);

colouring agents, for example conventional pharmaceutically acceptable dyes;

sweetening and flavouring agents;

preservatives; and other optional ingredients known in the art to permit production of oral dosage forms by known methods such as tabletting.

Solid oral dosage forms may be formulated in a manner known to those skilled in the art so as to give a sustained release of the compounds of the present invention. For example tablets or pills may, if desired, be provided with enteric coatings by known methods, for example by the use of cellulose acetate phthalate and/or hydroxypropylmethylcellulose phthalate.

Capsules or caplets, for example hard or soft gelatin capsules, containing the active compound with or without added excipients, for example a fatty oil, may be prepared by conventional means and, if desired, provided with enteric coatings in a known manner. The contents of the capsule or caplet may be formulated using known methods to give sustained release of the active compound. Enteric coated, solid oral dosage forms comprising compositions of the invention may be advantageous, depending on the nature of the active compound. Various materials, for example shellac and/or sugar, may be present as coatings, or to otherwise modify the physical form of the oral dosage form.

Liquid oral dosage forms comprising compositions of the invention may be elixirs, solutions, suspensions or syrups, for example, aqueous suspensions containing the active compound in an aqueous medium in the presence of a non-toxic suspending agent such as sodium carboxymethylcellulose; or oily suspensions containing a compound of the present invention in a suitable vegetable oil, for example arachis oil or sunflower oil. Liquid oral dosage forms may also comprise sweetening agents, flavouring agents and/or preservatives.

The active compound may be formulated into granules or powders with or without additional excipients. The granules or powders may be ingested directly by the patient or they may be added to a suitable liquid carrier (for example water) before ingestion. The granules or powders may contain disintegrants (for example a pharmaceutically acceptable effervescent couple formed from an acid and a carbonate or bicarbonate salt) to facilitate dispersion in the liquid medium.

Each of the above oral dosage forms may conveniently contain from about 1 mg to about 1000 mg of the active compound.

Compositions of the invention may be administered rectally in the known pharmaceutical forms for such administration, for example, suppositories with hard fat, semisynthetic glyceride, cocoa butter or polyethylene glycol bases.

Compositions of the invention may also be administered parenterally, for example by intravenous injection, in the known pharmaceutical forms for such administration, for example sterile suspensions in aqueous or oily media, or sterile solutions in a suitable solvent.

The active compound may also be administered by continuous infusion either from an external source, for example by intravenous infusion, or from a source of the compound placed within the body. Internal sources include implanted reservoirs containing the compound to be infused which is continuously released (for example by osmosis) or implants. Implants may be liquid, such as a suspension or solution in a pharmaceutically acceptable oil of the compound to be infused (for example in the form of a very sparingly water-soluble derivative such as a dodecanoate salt or ester). Implants may be solid in the form of an implanted support (for example a synthetic resin or waxy material) for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the active compound, or pharmaceutical compositions containing the active compound, in the form of particles of very small size, for example as obtained by fluid energy milling.

In the above compositions the active compound may, if desired, be associated with other compatible pharmacologically active ingredients.

A further aspect of the present invention provides use of compounds of formula I or II in the preparation of a medicament for the treatment of seizures and/or neurological disorders such as epilepsy and/or for neuroprotection to protect against conditions such as stroke.

A still further aspect of the present invention provides a method of treating seizures and/or neurological disorders such as epilepsy and/or a method of neuroprotection to protect against conditions such as stroke, which comprises the administration to patient in need thereof a therapeutically effective amount of compounds of formula I or II and/or a pharmaceutical compositions containing a therapeutically effective amount of compounds of formula I or II. Thus compounds of formula I or II are useful for the inhibition of seizures and/or neurological disorders such as epilepsy and/or as neuroprotective agents to protect against conditions such as stroke.

Whilst the precise amount of the active compound administered in the treatments outlined above will depend on a number of factors, for example the severity of the condition, the age and past medical history of the patient, and always lies within the sound discretion of the administering physician, a suitable daily dose of compounds of formula I or II for administration to human beings, is generally from about 1 mg to about 5000 mg, more usually from about 5 mg to about 1000 mg, given in a single dose or in divided doses at one or more times during the day. Oral administration is preferred.

Compounds of formula I or II may be used in adjunctive therapy with one or more other compounds having activity in the treatment of seizures and/or neurological disorders such as epilepsy and/or as neuroprotective agents to protect against conditions such as stroke. It will be appreciated that the term therapy as used herein includes prophylactic use of compounds of formula I or II and pharmaceutical compositions containing compounds of formula I or II, for example as neuroprotective agents to protect against conditions such as stroke or to prevent the onset of epileptic seizures. Compounds of formula I or II and pharmaceutical compositions containing compounds of formula I or II may be used to provide a local and/or systemic therapeutic effect.

The therapeutic activity of compounds of formula I or II has been demonstrated by means of tests in standard laboratory animals. Such tests include, for example, the tests of anticonvulsant activity in mice described below.

Processes for the preparation of compounds of formula I or II will now be described. These processes form a further aspect of the present invention.

Compounds of formula I or II, in which $R_3$ and $R_4$ are both H and $R_5$ is H or alkyl may be prepared by reducing a compound of formula III

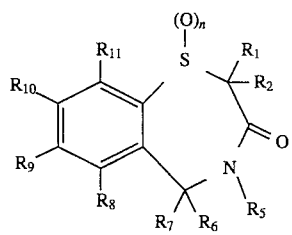
III in which $R_5$ is H or alkyl, with a reducing agent, for example lithium aluminium hydride or borane-dimethyl-sulphide complex. Compounds of formula III are known and can be prepared as described in international patent application WO 92/21668.

Compounds of formula I or II in which $R_3$ and $R_4$ together are a group of formula $=NR_{12}$ may be prepared by the reaction of compounds of formula IV

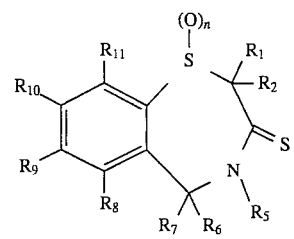
IV with a compound of formula $R_{12}NH_2$.

Compounds of formula I or II in which $R_3$ and $R_4$ together are a group of formula $=NR_{12}$ and $R_5$ is H may be prepared by the reaction of compounds of formula V

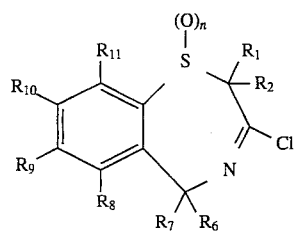
V with a compound of formula $R_{12}NH_2$.

Compounds of formula I or II in which $R_3$ and $R_4$ together are alkoxyimino may be prepared by the reaction between compounds of formula I or II in which $R_3$ and $R_4$ together are hydroxyimino with an alkylating agent such as an alkylsulphate.

Compounds of formula I or II in which $R_3$ and $R_4$ are H or alkyl and $R_5$ is alkyl may be prepared by alkylation of compounds of formula I or II in which $R_5$ is H for example; by using an alkylating agent such as an alkyl halide; or by reductive alkylation with an aldehyde or a ketone and formic acid, or a reducing agent such as sodium cyanoborohydride; or by reducing a compound of formula I or II in which $R_5$ is a group of formula $—COR_{13}$.

Compounds of formula I or II in which $R_5$ is a group of formula $—COR_{13}$ may be prepared by acylation of compounds of formula I or II in which n=0 or 2 and $R_5$ is H, for example with an acid chloride of formula $R_{13}COCl$, an acid anhydride of formula $(R_{13}CO)_2O$ or an acid of formula $R_{13}CO_2H$.

Compounds of formula I or II in which $R_5$ is a group of formula $—S(O)_pR_{14}$ may be prepared by the reaction of compounds of formula I or II in which $R_5$ is H, with a sulphonylating agent such as a sulphonyl chloride of formula $R_{14}SO_2Cl$, or a sulphinylating agent such as a sulphinyl chloride of formula $R_{14}SOCl$. For example, compounds of formula I or II in which $R_5$ is $—SO_2$Me may be prepared by the reaction of a compound of formula I or II in which $R_5$ is H with methanesulphonyl chloride.

Compounds of formula I or II in which n=1 may be prepared by the oxidation of compounds of formula I or II in which n=0, for example using sodium periodate or 3-chloroperbenzoic acid.

Compounds of formula I or II in which n=2 may be prepared by the oxidation of compounds of formula I or II in which n=0 or 1, for example using peracetic acid or 3-chloroperbenzoic acid.

Compounds of formula IV may be prepared by the reaction of compounds of formula III with reagents such as phosphorus pentasulphide or Lawesson's reagent [which is the known compound 2,4-bis(4-methoxyphenyl)-1,3-dithia-2,4-diphosphetane-2,4 disulphide].

Compounds of formula V may be prepared by the reaction of compounds of formula III with a chlorinating agent, for example phosphorus pentachloride or phosphoryl chloride.

The anticonvulsant activity of compounds of formula I or II was demonstrated by the following pharmacological tests.

Firstly, by observing the ability of the compound of formula I or II to antagonise the myoclonic seizures induced by the administration of (+)-bicuculline. Hereinafter, this test is referred to as 'BICM'.

In the BICM experiments groups of female mice in the weight range 25 to 30 grammes had free access to food and water until one hour before administration of the compound of formula I or II to be tested. The compound to be tested was orally administered at one or more doses in 1% aqueous methylcellulose solution. One hour later (+)-bicuculline at a dose of 0.55 mg/kg was administered intravenously into a tail vein. Such a dose of (+)-bicuculline would generally be expected to induce a seizure in the mice.

During the following two minutes the animals were observed and the percentage of animals in which seizures had been inhibited was recorded. Thus, the greater the anticonvulsant activity of the compound, the higher was the percentage recorded in the BICM test. If results at more than one dose were available, then a value for the dose inhibiting the seizures in 50% of the animals ($ED_{50}$) was calculated from the regression straight line plot of the percentage of animals in which seizures were inhibited against the dose of the compound of formula I or II administered.

The second test of anticonvulsant activity involved observing the ability of a compound to inhibit seizures in mice induced by a maximal electroshock. Hereinafter, this test is referred to as 'MESM'.

In the MESM experiments, groups of male mice in the weight range 25 to 30 grammes had free access to food and water until one hour before administration of the compound of formula I or II to be tested. The compound to be tested was orally administered at one or more doses in 1% aqueous methylcellulose solution. One hour later an electroshock of duration 1.0 second was administered to the mice through ear clip electrodes. The electroshock had an intensity of 99 mA, frequency of 50 Hz and pulse width of 0.4 ms. Such a shock would generally be expected to induce a seizure in the mice.

During the following two minutes the animals were observed and the percentage of animals in which seizures had been inhibited was recorded. Thus, the greater the anticonvulsant activity of the compound, the higher was the percentage recorded in the MESM test. If results at more than one dose were available, then a value for the dose inhibiting seizures in 50% of the animals ($ED_{50}$) was calculated from the regression straight line plot of the percentage of animals in which seizures were inhibited against the dose of the compound of formula I or II administered.

The compounds of formula I or II described hereinafter in Examples 1 to 31 have been found to have anticonvulsant activity in at least one of the BICM and MESM tests.

The invention will now be illustrated by the following non-limiting examples. The final product of each example was characterised by one or more of the following; elemental analysis; infra-red spectroscopy; nuclear magnetic resonance spectroscopy; and/or liquid chromatography. Temperatures are given in degrees Celsius.

EXAMPLE 1

6-Chloro-4,5-dihydro-1,4-benzothiazepin-3(2H)-one (9.8 g, prepared in a similar manner to example 11 of international patent application WO 92/21668) was added to a stirred solution of lithium aluminium hydride (5.01 g) in dry tetrahydrofuran (400 ml), After the addition, the reaction mixture was heated under reflux for five minutes and cooled. Excess lithium aluminium hydride was decomposed by adding a saturated aqueous solution of sodium sulphate. The mixture was filtered and the solvent removed from the filtrate by evaporation. The residue was dissolved in diethyl ether, acidified with hydrogen chloride gas and the precipitated 6-chloro-2,3,4,5-tetrahydro-1,4-benzothiazepine hydrochloride was collected by filtration, and was recrystallised from ethanol. Yield 6.5 g (m.p. 244°–246° C.).

The $ED_{50}$, in the BICM test described above, for this compound was 8.2 mg/kg.

EXAMPLE 2

6-Chloro-4,5-dihydro-1,4-benzothiazepin-3(2H)-one (9.8 g, prepared in a similar manner to example 11 of international patent application WO 92/21668) was added to a stirred solution of lithium aluminium hydride (5.01 g) in dry tetrahydrofuran (400 ml). After the addition, the reaction mixture was heated under reflux for five minutes and then cooled. Excess lithium aluminium hydride was decomposed by adding of a saturated aqueous solution of sodium sulphate. The mixture was filtered and the solvent evaporated from the filtrate to give 6-chloro-2,3,4,5-tetrahydro-1,4-benzothiazepine as an oil.

A solution of sodium periodate (3.09 g) in water (25 ml) was added dropwise with cooling to a stirred solution of 6-chloro-2,3,4,5-tetrahydro-1,4-benzothiazepine (2.88 g, prepared in a similar manner to that described in the preceding paragraph) in dichloromethane (75 ml). The stirring was continued at room temperature for 19 hours. Solvent was removed from the mixture by evaporation at reduced pressure. Purification of the residue by flash chromatography using dichloromethane/ethanol (95:5) as eluent gave 6-chloro-2,3,4,5-tetrahydro-1,4-benzothiazepine 1-oxide, which was recrystallised from ethyl acetate. Yield 2.15 g (m.p. 125°–126° C.).

The $ED_{50}$, in the BICM test described above, for this compound was 2.7 mg/kg.

EXAMPLE 3

6-Fluoro-4,5-dihydro-1,4-benzothiazepin-3 (2H) -one (9 g, prepared in a similar manner to example 5 of international patent application WO 92/21668) was added to a stirred solution of lithium aluminium hydride (5 g) in dry tetrahydrofuran (500 ml). After the addition, the reaction mixture was heated under reflux for ten minutes and cooled. Excess lithium aluminium hydride was decomposed by adding a saturated aqueous solution of sodium sulphate. The mixture was filtered and the solvent removed from the filtrate by evaporation to give an oil, which was dissolved in diethyl ether and acidified with hydrogen chloride gas. The precipitated 6-fluoro-2,3,4,5-tetrahydro-1,4-benzothiazepine hydrochloride was collected by filtration and was recrystallised from ethanol. Yield 7.43 g (m.p. 265°–68° C.).

The $ED_{50}$, in the BICM test described above, for this compound was 17.7 mg/kg.

EXAMPLE 4

6-Methyl-4,5-dihydro-1,4-benzothiazepin-3 (2H) -one (6 g, prepared in a similar manner to example 13 of international patent application WO 92/21668) was added to a stirred solution of lithium aluminium hydride (3.38 g) in dry tetrahydrofuran (340 ml). After the addition, the reaction mixture was heated under reflux for ten minutes, and cooled. Excess lithium aluminium hydride was decomposed by adding a saturated aqueous solution of sodium sulphate. The mixture was filtered and the solvent was removed from the filtrate by evaporation. The residue was dissolved in diethyl ether, acidified with hydrogen chloride gas and the precipitated 6-methyl-2,3,4,5-tetrahydro-1-1,4-benzothiazepine hydrochloride was collected by filtration and was recrystallised from ethanol. Yield 2.87 g (m.p. 248°–250° C.).

The $ED_{50}$, in the BICM test described above, for this compound was 66.5 mg/kg.

EXAMPLE 5

A solution of 6-chloro-4,5-dihydro-1,4-benzothiazepin-3(2H)-one (5.33 g, prepared in a similar manner to example 11 of international patent application WO 92/21668) in dry dimethylsulphoxide (60 ml) was added slowly at room temperature to a stirred suspension of sodium hydride (0.6 g) in dimethylsulphoxide (20 ml). After the addition was completed, the mixture was stirred for 30 minutes before adding methyl iodide (6 ml) dropwise. The reaction mixture was stirred at room temperature for one hour, water (160 ml) was added and the mixture was extracted with diethyl ether. The organic layer was washed with water and the solvent was removed by evaporation. Purification of the residue by flash chromatography using dichloromethane/ethyl acetate (9.8:0.2) as eluent gave 6-chloro-4-methyl-4,5-dihydro-1,4-benzothiazepin-3(2H)-one. Yield 3.8 g (m.p. 122°–125° C.).

6-Chloro-4-methyl-4,5-dihydro-1,4-benzothiazepin-3(2H)-one (3.8 g) was added to a stirred solution of lithium aluminium hydride (1.92 g) in dry tetrahydrofuran (160 ml). After the addition, the reaction was heated under reflux for 15 minutes and cooled. Excess lithium aluminium hydride was decomposed by adding a saturated aqueous solution of sodium sulphate. The mixture was filtered and the solvent was removed from the filtrate by evaporation. Purification of the residue by flash chromatography using dichloromethane/ethanol (9.5:0.5) as eluent gave an oil (2.62 g) which was dissolved in diethyl ether and acidified with hydrogen chloride gas. The precipitated 6-chloro-4-methyl-2,3,4,5-tetrahydro-1,4-benzothiazepine hydrochloride was collected by filtration and was recrystallised from ethanol/diethyl ether. Yield 2.38 g (m.p. 209°–211° C.).

In the BICM test described above, a dosage of 100 mg/kg of this compound inhibited 50% of the mice tested from seizures.

EXAMPLE 6

4,5-Dihydro-1,4-benzothiazepin-3(2H)-one (12 g, prepared in a similar manner to example 1 of international patent application WO 92/21668) was added to a stirred solution of lithium aluminium hydride (6.3 g) in dry tetrahydrofuran (400 ml). After the addition, the reaction mixture was heated under reflux for ten minutes and cooled. Excess of lithium aluminium hydride was decomposed by adding a saturated aqueous solution of sodium sulphate. The mixture was filtered and the solvent was removed from the filtrate by evaporation to give 2,3,4,5-tetrahydro-1,4-benzothiazepine as an oil which was used without further purification. Yield 9.4 g.

A mixture of 2,3,4,5-tetrahydro-1,4-benzothiazepine (4.56 g), formic acid (20 ml) and toluene (60 ml) was heated under reflux at 90° C. for four hours and then at 120° C. for a further three hours. The solvent was removed from the mixture by evaporation at reduced pressure. Purification of the residue by flash chromatography using dichloromethane as eluent gave 4-formyl-2,3,4,5-tetrahydro-1,4-benzothiazepine, which was recrystallised from hexane. Yield 3.73 g (m.p. 84°–87° C.).

The $ED_{50}$, in the BICM test described above, for this compound was 17.9 mg/kg.

EXAMPLE 7

A solution of 2,3,4,5-tetrahydro-1,4-benzothiazepine (1.5 g, prepared as described in the first paragraph of Example 6 above) in acetic anhydride (15 ml) was stirred at room temperature for one hour. The reaction mixture was poured into ice and extracted with dichloromethane. The organic layer was dried and the solvent removed by evaporation to give 4-acetyl-2,3,4,5-tetrahydro-1,4-benzothiazepine [a compound known as a Friedel Crafts catalyst from Example 46 of EP 368063 (Bayer)]. The product was recrystallised from hexane. Yield 1.55 g (m.p. 69°–70° C.).

The $ED_{50}$, in the BICM test described above, for this compound was 65.7 mg/kg.

EXAMPLE 8

A solution of 3-chloroperbenzoic acid (1.03 g) in dichloromethane (100 ml) was added dropwise with cooling from 0° C. to −2° C. to a stirred solution of 4-acetyl-2,3,4,5-tetrahydro-1,4-benzothiazepine (1.03 g, prepared as Example 7 above) in dichloromethane (50 ml). The reaction mixture was stirred for 15 minutes, then washed with water, dried and the solvent was removed by evaporation at reduced pressure. Purification of the residue by flash chromatography using dichloromethane/ethanol (9:1) as eluent gave 4-acetyl-2,3,4,5-tetrahydro-1,4-benzothiazepine 1-oxide, which was recrystallised from ethyl acetate. Yield 0.67 g (m.p. 156°–157° C.).

The $ED_{50}$, in the BICM test described above, for this compound was 37.8 mg/kg.

EXAMPLE 9

A solution of 6-chloro-2,3,4,5-tetrahydro-1,4-benzothiazepine (1.6 g, prepared in a similar manner to its hydrochloride, Example 1 above) in acetic anhydride (15 ml) was stirred at room temperature for one hour. The reaction mixture was poured into ice and extracted with dichloromethane. The organic layer was dried and the solvent was removed by evaporation to give 4-acetyl-6-chloro-2,3,4,5-tetrahydro-1,4-benzothiazepine, which was recrystallised from hexane. Yield 1.68 g (m.p. 79°–81° C.).

The $ED_{50}$, in the BICM test described above, for this compound was 4.6 mg/kg.

The $ED_{50}$, in the MESM test described above, for this compound was 48.5 mg/kg.

EXAMPLE 10

A solution of 3-chloroperbenzoic acid (1.14 g) in dichloromethane (100 ml) was added dropwise with cooling from 0° C. to −2° C. to a stirred solution of 4-acetyl-6-chloro-2,3,4,5-tetrahydro-1,4-benzothiazepine (1.34 g, prepared as Example 9 above) in dichloromethane (50 ml). The reaction mixture was stirred for 15 minutes, washed with water, dried and the solvent was removed by evaporation at reduced pressure. Purification of the residue by flash chromatography using dichloromethane/ethanol (95:5) as eluent gave 4-acetyl-6-chloro-2,3,4,5-tetrahydro-1,4-benzothiazepine 1-oxide, which was recrystallised from ethyl acetate. Yield 1.15 g (m.p. 119°–121° C.).

The $ED_{50}$, in the BICM test described above, for this compound was 22.6 mg/kg.

The $ED_{50}$, in the MESM test described above, for this compound was 52.8 mg/kg.

EXAMPLE 11

A solution of 6-fluoro-2,3,4,5-tetrahydro-1,4-benzothiazepine (2.04 g, prepared in a similar manner to its hydrochloride, Example 3 above) in acetic anhydride (22 ml) was stirred at room temperature for one hour. The reaction mixture was poured into ice and extracted with dichloromethane. The organic layer was dried and the solvent removed by evaporation. Purification of the residue by flash chromatography using dichloromethane/ethanol (97:3) as eluent gave 4-acetyl-6-fluoro-2,3,4,5-tetrahydro-1,4-benzothiazepine as an oil. Yield 1.7 g.

The $ED_{50}$, in the BICM test described above, for this compound was 21.5 mg/kg.

EXAMPLE 12

A solution of 6-methyl-2,3,4,5-tetrahydro-1,4-benzothiazepine (0.91 g, prepared in a similar manner to its hydrochloride, Example 4 above) in acetic anhydride (10 ml) was stirred at room temperature for one hour. The reaction mixture was poured into ice and extracted with dichloromethane. The organic layer was dried and the solvent removed by evaporation to give 4-acetyl-6-methyl-2,3,4,5-tetrahydro-1,4-benzothiazepine, which was recrystallised from hexane. Yield 0.93 g (m.p. 71°–73° C.).

The $ED_{50}$, in the BICM test described above, for this compound was 49.4 mg/kg.

In the MESM test described above, a dosage of 100 mg/kg of this compound inhibited 50% of the mice tested from seizures.

EXAMPLE 13

A solution of propionyl chloride (2.39 g) in dichloromethane (50 ml) was added dropwise at room temperature to a stirred solution of 2,3,4,5-tetrahydro-1,4-benzothiazepine (8.58 g, prepared as described in the first paragraph of Example 6 above) in dichloromethane (100 ml). The reaction mixture was stirred at room temperature for 45 minutes, washed with water, dried and the solvent was removed by evaporation. Purification of the residue by flash chromatography using dichloromethane/ethanol (98:2) as eluent gave 4-propionyl-2,3,4,5-tetrahydro-1,4-benzothiazepine as an oil. Yield 2.9 g.

The $ED_{50}$, in the BICM test described above, for this compound was 48.1 mg/kg.

EXAMPLE 14

A solution of propionyl chloride (0.92 g) in dichloromethane (10 ml) was added dropwise at room temperature to a stirred solution of 6-chloro-2,3,4,5-tetrahydro-1,4-benzothiazepine (1.99 g, prepared in a similar manner to its hydrochloride, Example 1 above) and triethylamine (1.01 g) in dichloromethane (50 ml). The reaction mixture was stirred at room temperature for 30 minutes, washed with water, dried and the solvent was removed by evaporation. Purification of the residue by flash chromatography using dichloromethane as eluent gave 6-chloro-4-propionyl-2,3,4, 5-tetrahydro-1,4-benzothiazepine, which was recrystallised from hexane. Yield 1.14 g (m.p. 55°–57° C.).

The $ED_{50}$, in the BICM test described above, for this compound was 44.7 mg/kg.

EXAMPLE 15

A solution of benzoyl chloride (3.93 g) in dichloromethane (50 ml) was added dropwise at room temperature to a stirred solution of 6-chloro-2,3,4,5-tetrahydro-1,4-benzothiazepine (4.5 g, prepared in a similar manner to its hydrochloride, Example 1 above) and triethylamine (2.82 g) in dichloromethane (100 ml). The reaction mixture was stirred at room temperature for 15 minutes, washed with water, dried and the solvent was removed by evaporation. Purification of the residue by flash chromatography using dichloromethane as eluent gave 4-benzoyl-6-chloro-2,3,4,5-tetrahydro-1,4-benzothiazepine, which was recrystallised from ethanol/water. Yield 5.93 g (m.p. 64°–72° C.).

The $ED_{50}$, in the BICM test described above, for this compound was 49.2 mg/kg.

EXAMPLE 16

A solution of methanesulphinyl chloride (0.98 g) in dichloromethane (10 ml) was added dropwise at room temperature to a stirred solution of 6-chloro-2,3,4,5-tetrahydro- 1,4-benzothiazepine (1.99 g, prepared in a similar manner to its hydrochloride, Example 1 above) and triethylamine (1.01 g) in dichloromethane (50 ml). The reaction mixture was stirred at room temperature for one hour, washed with water, dried and the solvent was removed by evaporation. Purification of the residue by flash chromatography using dichloromethane/ethanol (98:2) as eluent gave 6-chloro-4-methylsulphinyl-2,3,4,5-tetrahydro-1,4-benzothiazepine, which was recrystallised from ethylacetate/hexane. Yield 2.1 g (m.p. 82°–84° C.).

The $ED_{50}$, in the BICM test described above, for this compound was 19.6 mg/kg.

EXAMPLE 17

A solution of methanesulphonyl chloride (3.3 g) in dichloromethane (15 ml) was added dropwise at room temperature to a stirred solution of 2,3,4,5-tetrahydro-1,4-benzothiazepine (4.8 g, prepared as described in the first paragraph of Example 6 above) and triethylamine (2.9 g) in dichloromethane (100 ml). The reaction mixture was stirred at room temperature for one hour, washed with water, dried and the solvent was removed by evaporation. Purification of the residue by flash chromatography using dichloromethane as eluent gave 4-methylsulphonyl-2,3,4,5-tetrahydro-1,4-benzothiazepine which was recrystallised from hexane. Yield 3 g. (m.p. 98°–100° C.).

The $ED_{50}$, in the BICM test described above, for this compound was 40.8 mg/kg.

The $ED_{50}$, in the MESM test described above, for this compound was 51.6 mg/kg.

EXAMPLE 18

A solution of 3-chloroperbenzoic acid (1.4 g) in dichloromethane (200 ml) was added dropwise with cooling from 0° C. to −2° C. to a stirred solution of 4-methylsulphonyl-2,3,4,5-tetrahydro-1,4-benzothiazepine (2 g, prepared as Example 17 above) in dichloromethane (50 ml). The reaction mixture was stirred for 15 minutes, washed with water, dried and the solvent was removed by evaporation at reduced pressure. Purification of the residue by flash chromatography using dichloromethane/ethanol (95:5) as eluent gave 4-methylsulphonyl-2,3,4,5-tetrahydro-1,4-benzothiazepine 1-oxide, which was recrystallised from ethanol. Yield 1.65 g (m.p. 195°–197° C.).

The $ED_{50}$, in the BICM test described above, for this compound was 27.4 mg/kg.

EXAMPLE 19

A solution of methanesulphonyl chloride (3.43 g) in dichloromethane (30 ml) was added dropwise at room temperature to a stirred solution of 6-chloro-2,3,4,5-tetrahydro-1,4-benzothiazepine (5.2 g, prepared in a similar manner to its hydrochloride, Example 1 above) and triethylamine (3.03 g, 0.03 ml) in dichloromethane (100 ml). The reaction mixture was stirred at room temperature for one hour, washed with water, dried and the solvent was removed by evaporation. Purification of the residue by flash chromatography using dichloromethane as eluent gave 6-chloro-4-methylsulphonyl-2,3,4,5-tetrahydro-1,4-benzothiazepine, which was recrystallised from hexane. Yield 6.06 g (m.p. 85°–86° C.).

The $ED_{50}$, in the BICM test described above, for this compound was 41.3 mg/kg.

The $ED_{50}$, in the MESM test described above, for this compound was 19.5 mg/kg.

EXAMPLE 20

A solution of 3-chloroperbenzoic acid (2.26 g) in dichloromethane (150 ml) was added dropwise with cooling from 0° C. to −2° C. to a stirred solution of 6-chloro-4-methylsulphonyl-2,3,4,5-tetrahydro-1,4-benzothiazepine (3.05 g, prepared as Example 19 above) in dichloromethane (100 ml). The reaction mixture was stirred for 15 minutes, washed with water and dried, and the solvent was removed by evaporation at reduced pressure. Purification of the residue by flash chromatography using dichloromethane/ethanol (95:5) as eluent gave 6-chloro-4-methylsulphonyl-2,3,4,5-tetrahydro-1,4-benzothiazepine 1-oxide, which was recrystallised from ethyl acetate. Yield 2.86 g (m.p. 167°–169° C.).

The $ED_{50}$, in the BICM test described above, for this compound was 36.2 mg/kg.

The $ED_{50}$, in the MESM test described above, for this compound was 31.9 mg/kg.

EXAMPLE 21

A solution of methanesulphonyl chloride (1.83 g) in dichloromethane (30 ml) was added dropwise at room temperature to a stirred solution of 6-fluoro-2,3,4,5-tetrahydro-1,4-benzothiazepine (2.65 g, prepared in a similar manner to its hydrochloride, Example 3 above) and triethylamine (1.6 g) in dichloromethane (60 ml). The reaction mixture was stirred at room temperature for 20 minutes, washed with water, dried and the solvent was removed by evaporation. Purification of the residue by flash chromatography using dichloromethane as eluent gave 6-fluoro-4-methylsulphonyl-2,3,4,5-tetrahydro-1,4-benzothiazepine, which was recrystallised from hexane. Yield 3.3 g (m.p. 115°–117° C.).

The $ED_{50}$, in the BICM test described above, for this compound was 33.8 mg/kg.

The $ED_{50}$, in the MESM test described above, for this compound was 30.5 mg/kg.

EXAMPLE 22

A solution of methanesulphonyl chloride (1.69 g) in dichloromethane (20 ml) was added dropwise at room temperature to a stirred solution to 6-methyl-2,3,4,5-tetrahydro-1,4-benzothiazepine (2 g, prepared in a similar manner to its hydrochloride, Example 4 above) and triethylamine (1.51 g) in dichloromethane (30 ml). The reaction mixture was stirred at room temperature for one hour, washed with water, dried and the solvent was removed by evaporation. Purification of the residue by flash chromatography using dichloromethane as eluent gave 6-methyl-4-methylsulphonyl-2,3,4,5-tetrahydro-1,4-benzothiazepine, which was recrystallised from ethyl acetate/hexane. Yield 2.48 g (m.p. 128°–130° C.).

The $ED_{50}$, in the BICM test described above, for this compound was 116.3 mg/kg.

The $ED_{50}$, in the MESM test described above, for this compound was 102.2 mg/kg.

EXAMPLE 23

A solution of ethanesulphonyl chloride (3.8 g) in dichloromethane (50 ml) was added dropwise at room temperature to a stirred solution of 2,3,4,5-tetrahydro-1,4-benzothiazepine (4.29 g, prepared as described in the first paragraph of Example 6 above) in dichloromethane (100 ml). The reaction mixture was stirred at room temperature for one hour, washed with water, dried and the solvent was removed by evaporation. Purification of the residue by flash chromatography using trichloromethane as eluent gave 4-ethylsulphonyl-2,3,4,5-tetrahydro-1,4-benzothiazepine, which was recrystallised from hexane. Yield 4.25 g (m.p. 78°–80° C.).

The $ED_{50}$, in the MESM test described above, for this compound was 22.3 mg/kg.

EXAMPLE 24

A solution of ethanesulphonyl chloride (1.28 g) in dichloromethane (10 ml) was added dropwise at room temperature to a stirred solution of 6-chloro-2,3,4,5-tetrahydro-1,4-benzothiazepine (1.99 g, prepared in a similar manner to its hydrochloride, Example 1 above) and triethylamine (1.01 g) in dichloromethane (50 ml). The reaction mixture was stirred at room temperature for one hour, washed with water, dried and the solvent was removed by evaporation. Purification of the residue by flash chromatography using dichloromethane as eluent gave 4-ethylsulphonyl-6-chloro-2,3,4,5-tetrahydro-1,4-benzothiazepine, which was recrystallised from ethyl acetate/hexane. Yield 2.53 g (m.p. 126°–128° C.).

The $ED_{50}$, in the BICM test described above, for this compound was 90.4 mg/kg.

The $ED_{50}$, in the MESM test described above, for this compound was 35.1 mg/kg.

EXAMPLE 25

A stirred mixture of 4,5-dihydro-1,4-benzothiazepin-3(2H)-one (1.79 g, prepared as example 1 of international patent application WO 92/21668) and Lawesson's reagent (2.22 g) in dry toluene (100 ml) was heated at 100° C. for three hours. The mixture was allowed to cool to room temperature. The precipitated solid was collected by filtration, washed with toluene and dried to give 4,5-dihydro-1,4-benzothiazepin-3(2H)-thione. Yield 1.78 g (m.p. 215°–219° C.).

A mixture of 4,5-dihydro-1,4-benzothiazepin-3(2H)-thione (1.56 g), hydroxylamine hydrochloride (0.83 g) and sodium acetate (0.98 g) in dry ethanol (100 ml) was heated under reflux for three hours. The mixture was cooled, and the precipitated solid was collected by filtration and washed with water. Purification of the precipitate by flash chromatography using dichloromethane/ethanol (95:5) as eluent gave 3-hydroxyimino-2,3,4,5-tetrahydro-1,4-benzothiazepine, which was recrystallised from ethanol. Yield 1.2 g (m.p. 208°–210° C.).

The $ED_{50}$, in the BICM test described above, for this compound was 31.5 mg/kg.

EXAMPLE 26

A stirred mixture of 6-chloro-4,5-dihydro-1,4-benzothiazepin-3(2H)-one (4.27 g, prepared as example 11 of international patent application WO 92/21668) and Lawesson's reagent (4.90 g) in dry toluene (170 ml) was heated under reflux for one hour. The reaction mixture was cooled to room temperature and the precipitated 6-chloro-4,5-dihydro-1,4-benzothiazepin-3(2H)-thione was collected by filtration, washed with toluene and dried. Yield 4.16 g (m.p. 210°–212° C.).

A stirred mixture of 6-chloro-4,5-dihydro-1,4-benzothiazepin-3(2H)-thione (3.90 g), hydroxylamine hydrochloride (1.77 g) and sodium acetate (2.09 g) in dry ethanol (175 ml) was heated under reflux for one hour. The reaction mixture was cooled and the precipitated 6-chloro-3-hydroxyimino-2,3,4,5-tetrahydro-1,4-benzothiazepine was collected by filtration, washed with water and recrystallised from ethanol. Yield 2.6 g (m.p. 180°–183° C.).

The $ED_{50}$, in the BICM test described above, for this compound was 5.0 mg/kg.

EXAMPLE 27

A stirred mixture of 6-methyl-4,5-dihydro-1,4-benzothiazepin-3(2H)-one (3.26 g, prepared in a similar manner to example 13 of international patent application WO 92/21668) and Lawesson's reagent (3.93 g) in dry toluene (170 ml) was heated under reflux for one hour. The reaction mixture was cooled to room temperature and the precipitated 6-methyl-4,5-dihydro-1,4-benzothiazepin-3(2H)-thione was collected by filtration, washed with toluene and dried. Yield 3.30 g (m.p. 228°–230° C.).

A stirred mixture of 6-methyl-4,5-dihydro-1,4-benzothiazepin-3(2H)-thione (3.13 g), hydroxylamine hydrochloride (1.56 g) and sodium acetate (1.84 g) in dry ethanol (175 ml) was heated under reflux for one hour. The reaction mixture was cooled and the precipitated 3-hydroxyimino-6-methyl-2,3,4,5-tetrahydro-1,4-benzothiazepine was collected by filtration, washed with water and recrystallised from ethanol. Yield 2.23 g (m.p. 188°–190° C.).

The $ED_{50}$, in the BICM test described above, for this compound was 20.1 mg/kg.

EXAMPLE 28

Dimethylsulphate (1.26 g) was added dropwise to a vigorously stirred suspension of 3-hydroxyimino-2,3,4,5-tetrahydro-1,4-benzothiazepine (2 g, prepared in a similar manner to Example 25 above) in a mixture of a 10% aqueous solution of sodium hydroxide (4 ml) and ethanol (150 ml). The reaction mixture was kept at room temperature for 24 hours and then extracted with dichloromethane. The organic layer was dried and the solvent was removed by evaporation. Purification of the solid residue by flash chromatography using dichloromethane as eluent gave 3-methoxyimino-2,3,4,5-tetrahydro-1,4-benzothiazepine, which was recrystallised from hexane. Yield 1.51 g (m.p. 101°–102° C.).

The $ED_{50}$, in the BICM test described above, for this compound was 58.2 mg/kg.

EXAMPLE 29

A 10% aqueous solution of sodium hydroxide (4 ml) was added to a suspension of 6-chloro-3-hydroxyimino-2,3,4,5-tetrahydro-1,4-benzothiazepine (2.29 g, prepared as Example 26 above) in ethanol (150 ml). After 15 minutes dimethylsulphate (1.33 g) was added dropwise to the mixture. The reaction mixture was stirred at room temperature for 22 hours and then the solvent was removed by evaporation at reduced pressure. Purification of the residue by chromatography on a silica gel support using dichloromethane followed by dichloromethane/ethanol (97:3) as successive eluents gave 6-chloro-3-methoxyimino-2,3,4,5-tetrahydro-1,4-benzothiazepine, which was recrystallised from n-hexane. Yield 1.21 g (m.p. 120°–121° C.).

In the BICM test described above, a dosage of 100 mg/kg of this compound inhibited 50% of the mice tested from seizures.

EXAMPLE 30

A mixture of 4,5-dihydro-1,4,-benzothiazepine-3(2H)-one (5.37 g, prepared as example 1 of international patent application WO 92/21668) and phosphorus pentachloride (6.3 g) in dry toluene was heated at 50° C. for two hours. The precipitated product was collected by filtration, washed with toluene and dried to give 3-chloro-2,5-dihydro-1,4-benzothiazepine. Yield 5.2 g (m.p. 164°–168° C.). This crude product was used in the next step without further purification.

3-Chloro-2,5-dihydro-1,4-benzothiazepine (5 g) and a 33% solution of methylamine in absolute ethanol (150 ml) were heated under reflux for one hour. The mixture was cooled and filtered. Purification of the residue by flash chromatography using ethyl acetate/ethanol (1:1) as eluent gave 3-methylimino-2,3,4,5-tetrahydro-1,4-benzothiazepine, which was recrystallised from ethanol. Yield 0.51 g (m.p. 278°–280° C.).

The $ED_{50}$, in the BICM test described above, for this compound was 20.8 mg/kg.

EXAMPLE 31

Phosphorus pentachloride (5.84 g) was added in portions to a stirred suspension of 6-chloro-4,5-dihydro-1,4-benzothiazepin-3(2H)-one (6.0 g, prepared as example 1 of international patent application WO 92/21668) in dry toluene (450 ml). The reaction mixture was then heated in an oil bath at 50°–60° C. for 5½ hours. After cooling, the crude precipitate of 3,6-dichloro-2,5-dihydro-1,4-benzothiazepine was collected by filtration, and washed with toluene. Yield 4.85 g. This crude product was used in the next step without further purification.

A solution of aniline (4.8 ml) in dry ethanol (10 ml) was added dropwise at room temperature to a stirred solution of 3,6-dichloro-2,5-dihydro-1,4-benzothiazepine (2.5 g) in dry ethanol (65 ml). The reaction mixture was heated under reflux for 9½ hours, cooled to room temperature, filtered and the solvent was removed from the filtrate by evaporation at reduced pressure. The oily residue was separated into fractions by chromatography on a silica gel support using chloroform/ethanol (50:1) as eluent. Purification of those fractions containing the product by flash chromatography using ethyl acetate/hexane (2:3) as eluent gave 6-chloro-3-phenylimino-2,3,4,5-tetrahydro-1,4-benzothiazepine, which was recrystallised from ethyl acetate/hexane. Yield 0.27 g (m.p. 150°–152° C.).

The $ED_{50}$, in the BICM test described above, for this compound was 16.3 mg/kg.

We claim:

1. A compound of formula I

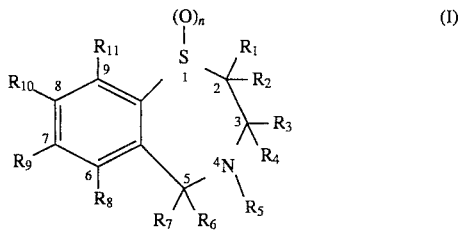

wherein n is 0, 1 or 2;

$R_1$, $R_2$, $R_6$ and $R_7$ are H;

$R_3$ and $R_4$ are independently H or methyl; or together are selected from the group consisting of imino, methylimino, phenylimino, hydroxyimino and methoxyimino;

$R_5$ is H or methyl, or when $R_3$ and $R_4$ are independently H or methyl, $R_5$ is selected from the group consisting of formyl, acetyl, propionyl, benzoyl, methylsulphinyl, methylsulphonyl and ethylsulphonyl;

$R_8$ is selected from the group consisting of H, methyl, fluoro and chloro; and $R_9$, $R_{10}$ and $R_{11}$ are each H, a stereoisomer thereof or a pharmaceutically acceptable salt thereof;

with the provisos that i) at least one of $R_1$ to $R_{11}$ is other than H;

ii) when n is 0 and $R_1$ to $R_4$ and $R_6$ to $R_{11}$ are each H, then $R_5$ is other than benzoyl or acetyl; and iii) when n is 0, 1 or 2, and $R_1$ to $R_3$ and $R_5$ to $R_{11}$ are each H, then $R_4$ is other than methyl.

2. A compound as claimed in claim 1, wherein the compound is selected from:

6-chloro-2,3,4,5-tetrahydro-1,4-benzothiazepine;

6-chloro-2,3,4,5-tetrahydro-1,4-benzothiazepine 1-oxide;

6-fluoro-2,3,4,5-tetrahydro-1,4-benzothiazepine;

4-formyl-2,3,4,5-tetrahydro-1,4-benzothiazepine;

4-acetyl-6-chloro-2,3,4,5-tetrahydro-1,4-benzothiazepine;

4-acetyl-6-chloro-2,3,4,5-tetrahydro-1,4-benzothiazepine 1-oxide;

4-acetyl-6-fluoro-2,3,4,5-tetrahydro-1,4-benzothiazepine;

6-chloro-4-methylsulphinyl-2,3,4,5-tetrahydro-1,4-benzothiazepine;

4-methylsulphonyl-2,3,4,5-tetrahydro-1,4-benzothiazepine oxide;

4-ethylsulphonyl-2,3,4,5-tetrahydro-1,4-benzothiazepine;

6-chloro-3-hydroxyimino-2,3,4,5-tetrahydro-1,4-benzothiazepine;

3-hydroxyimino-6-methyl-2,3,4,5-tetrahydro-1,4-benzothiazepine;

3-methylimino-2,3,4,5-tetrahydro-1,4-benzothiazepine; and 6-chloro-3-phenylimino-2,3,4,5-tetrahydro-1,4-benzothiazepine, a stereoisomer thereof, or a pharmaceutically acceptable salt thereof.

3. A compound as claimed in claim 1, wherein the compound is selected from:

6-chloro-2,3,4,5-tetrahydro-1,4-benzothiazepine;

6-chloro-2,3,4,5-tetrahydro-1,4-benzothiazepine 1-oxide;

6-fluoro-2,3,4,5-tetrahydro-1,4-benzothiazepine;

4-formyl-2,3,4,5-tetrahydro-1,4-benzothiazepine;

4-acetyl-6-chloro-2,3,4,5-tetrahydro-1,4-benzothiazepine;

6-chloro-4-methylsulphinyl-2,3,4,5-tetrahydro-1,4-benzothiazepine;

6-chloro-3-hydroxyimino-2,3,4,5-tetrahydro-1,4-benzothiazepine; and 6-chloro-3-phenylimino-2,3,4,5-tetrahydro-1,4-benzothiazepine, a stereoisomer thereof, or a pharmaceutically acceptable salt thereof.

4. A compound as claimed in claim 1, wherein the compound is selected from:

4-acetyl-6-chloro-2,3,4,5-tetrahydro-1,4-benzothiazepine;

4-acetyl-6-chloro-2,3,4,5-tetrahydro-1,4-benzothiazepine 1-oxide;

4-methylsulphonyl-2,3,4,5-tetrahydro-1,4-benzothiazepine;

6-chloro-4-methylsulphonyl-2,3,4,5-tetrahydro-1,4-benzothiazepine;

6-chloro-4-methylsulphonyl-2,3,4,5-tetrahydro-1,4-benzothiazepine 1-oxide; and 6-fluoro-4-methylsulphonyl-2,3,4,5-tetrahydro-1,4-benzothiazepine, a stereoisomer thereof, or a pharmaceutically acceptable salt thereof.

5. A compound as claimed in claim 1, wherein the compounds is:

4-acetyl-6-chloro-2,3,4,5-tetrahydro-1,4-benzothiazepine, a stereoisomer thereof, or a pharmaceutically acceptable salt thereof.

6. A pharmaceutical composition comprising a compound of formula I

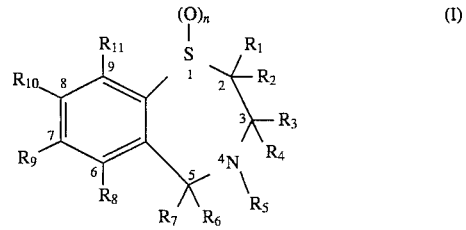

wherein n=0, 1 or 2;

$R_1$ and $R_2$ independently are H or alkyl of 1 to 4 carbon atoms which is unsubstituted or substituted by at least one halo atom;

$R_3$ and $R_4$ independently are H or alkyl of 1 to 4 carbon atoms; or together represent a group of formula $=NR_{12}$ where $R_{12}$ is selected from the group consisting of H, hydroxy, alkyl of 1 to 4 carbon atoms, phenyl and alkoxy of 1 to 4 carbon atoms; wherein each alkyl, phenyl and alkoxy is unsubstituted or substituted by at least one halo atom;

$R_5$ is selected from the group consisting of (a) H, (b) alkyl of 1 to 4 carbon atoms, (c) a group of formula —$COR_{13}$ wherein $R_{13}$ is selected from the group consisting of H, alkyl of 1 to 4 carbon atoms and phenyl, when $R_3$ and $R_4$ independently are H or alkyl of 1 to 4 carbon atoms which is unsubstituted or substituted by at least one halo atom and (d) a group of formula —$S(O)_pR_{14}$ in which p=1 or 2 and $R_{14}$ is alkyl of 1 to 4 carbon atoms or phenyl, when $R_3$ and $R_4$ independently are H or alkyl of 1 to 4 carbon atoms which is unsubstituted or substituted by one or more halo atom; wherein each alkyl and phenyl is unsubstituted or substituted by at least one halo atom;

$R_6$ and $R_7$ independently are H;

$R_8$ to $R_{11}$ independently are selected from the group consisting of H, halo, cyano, nitro, alkyl of 1 to 4 carbon atoms, alkoxy of 1 to 4 carbon atoms, alkanoyl of 1 to 4 carbon atoms, carboxy, alkanoyloxy of 1 to 4 carbon atoms, carbamoyl which is unsubstituted or substituted with alkyl of 1 to 4 carbon atoms and sulphamoyl which is unsubstituted or substituted with alkyl of 1 to 4 carbon atoms; wherein each alkyl, alkoxy, alkanoyl or alkanoyloxy is unsubstituted or substituted by at least one halo atom, a stereoisomer thereof, or a pharmaceutically acceptable salt thereof, with the proviso that:

(i) when n=0; at least one of $R_1$ to $R_{11}$ is other than H; together with a pharmaceutically acceptable diluent or carrier.

7. A pharmaceutical composition as claimed in claim 6, wherein n=0 or 1;

$R_1$ and $R_2$ are independently H or methyl;

$R_3$ and $R_4$ are independently H or methyl; or together are selected from the group consisting of imino, methylimino, phenylimino, hydroxyimino and methoxyimino;

$R_5$ is H or methyl, or when $R_3$ and $R_4$ are independently H or methyl, $R_5$ is selected from the group consisting of formyl, acetyl, propionyl, benzoyl, methylsulphinyl, methylsulphonyl and ethylsulphonyl;

$R_6$ and $R_7$ independently are H; and one of $R_8$ to $R_{11}$ is (a) H, (b) fluoro, (c) chloro, (d) bromo, (e) iodo, (f) methyl which is unsubstituted or substituted with one or more halo, (g) methoxy which is unsubstituted or substituted by one or more halo, (h) nitro, (i) cyano, (j) carboxy, (k) acetyl, (l) dimethylcarbamoyl and (m) dimethylsulphamoyl; and the remainder of $R_8$ to $R_{11}$ are H, a stereoisomer thereof, or a pharmaceutically acceptable salt thereof.

8. A pharmaceutical composition as claimed in claim 6, wherein n=0 or 1;

$R_1$, $R_2$, $R_6$ and $R_7$ are all H;

$R_3$ and $R_4$ are each H, or together are selected from the group consisting of methylimino, phenylimino, hydroxyimino or methoxyimino;

$R_5$ is H or methyl, or when $R_3$ and $R_4$ are each H, $R_5$ is selected from the group consisting of formyl, acetyl, propionyl, benzoyl, methylsulphinyl, methylsulphonyl and ethylsulphonyl;

$R_8$ is selected from the group consisting of H, methyl, fluoro and chloro; and $R_9$ to $R_{11}$ are all H, a stereoisomer thereof, or a pharmaceutically acceptable salt thereof.

9. A pharmaceutical composition as claimed in claim 6, wherein the compound is selected from:

6-chloro-2,3,4,5-tetrahydro-1,4-benzothiazepine;

6-chloro-2,3,4,5-tetrahydro-1,4-benzothiazepine 1-oxide;

6-fluoro-2,3,4,5-tetrahydro-1,4-benzothiazepine;

6-methyl-2,3,4,5-tetrahydro-1,4-benzothiazepine;

6-chloro-4-methyl-2,3,4,5-tetrahydro-1,4-benzothiazepine;

4-formyl-2,3,4,5-tetrahydro-1,4-benzothiazepine;

4-acetyl-2,3,4,5-tetrahydro-1,4-benzothiazepine;

4-acetyl-2,3,4,5-tetrahydro-1,4-benzothiazepine 1-oxide;

4-acetyl-6-chloro-2,3,4,5-tetrahydro-1,4-benzothiazepine;

4-acetyl-6-chloro-2,3,4,5-tetrahydro-1,4-benzothiazepine 1-oxide;

4-acetyl-6-fluoro-2,3,4,5-tetrahydro-1,4-benzothiazepine;

4-acetyl-6-methyl-2,3,4,5-tetrahydro-1,4-benzothiazepine;

4-propionyl-2,3,4,5-tetrahydro-1,4-benzothiazepine;

6-chloro-4-propionyl-2,3,4,5-tetrahydro-1,4-benzothiazepine;

4-benzoyl-6-chloro-2,3,4,5-tetrahydro-1,4-benzothiazepine;

6-chloro-4-methylsulphinyl-2,3,4,5-tetrahydro-1,4-benzothiazepine;

4-methylsulphonyl-2,3,4,5-tetrahydro-1,4-benzothiazepine;

4-methylsulphonyl-2,3,4,5-tetrahydro-1,4-benzothiazepine 1-oxide;

6-chloro-4-methylsulphonyl-2,3,4,5-tetrahydro-1,4-benzothiazepine;

6-chloro-4-methylsulphonyl-2,3,4,5-tetrahydro-1,4-benzothiazepine 1-oxide;

6-fluoro-4-methylsulphonyl-2,3,4, 5-tetrahydro-1,4-benzothiazepine;

6-methyl-4-methylsulphonyl-2,3,4,5-tetrahydro-1,4-benzothiazepine;

4-ethylsulphonyl-2,3,4,5-tetrahydro-1,4-benzothiazepine;

6-chloro-4-ethylsulphonyl-2,3,4,5-tetrahydro-1,4-benzothiazepine;

3-hydroxyimino-2,3,4,5-tetrahydro-1,4-benzothiazepine;

6-chloro-3-hydroxyimino-2,3,4,5-tetrahydro-1,4-benzothiazepine;

3-hydroxyimino-6-methyl-2,3,4,5-tetrahydro-1,4-benzothiazepine;

3-methoxyimino-2,3,4,5-tetrahydro-1,4-benzothiazepine;

6-chloro-3-methoxyimino-2,3,4,5-tetrahydro-1,4-benzothiazepine;

3-methylimino-2,3,4,5-tetrahydro-1,4-benzothiazepine; and 6-chloro-3-phenylimino-2,3,4,5-tetrahydro-1,4-benzothiazepine, a stereoisomer thereof or a pharmaceutically acceptable salt thereof.

10. A pharmaceutical composition as claimed in claim 6, wherein the compound is present in the composition in an amount from about 1 mg to about 1000 mg.

11. A method of treating seizures in a patient in need of such treatment, comprising administering to the patient a seizure-treating effective amount of a pharmaceutical composition as claimed in claim 6.

12. A method as claimed in claim 11, wherein the pharmaceutical composition is administered at a daily dose of from about 1 mg to about 5000 mg.

13. A method as claimed in claim 11, wherein the pharmaceutical composition is administered at a daily dose of from about 5 mg to about 1000 mg.

14. A method of treating a neurological disorder in a patient in need of such treatment, comprising administering to the patient a neurological-disorder-treating effective amount of a pharmaceutical composition as claimed in claim 6.

15. A method as claimed in claim 14, wherein the pharmaceutical composition is administered at a daily dose of from about 1 mg to about 5000 mg.

16. A method as claimed in claim 14, wherein the pharmaceutical composition is administered at a daily dose of from about 5 mg to about 1000 mg.

17. A method of treating epilepsy in a patient in need of such treatment, comprising administering to the patient a epilepsy-treating effective amount of a pharmaceutical composition as claimed in claim 6.

18. A method as claimed in claim 17, wherein the pharmaceutical composition is administered at a daily dose of from about 1 mg to about 5000 mg.

19. A method as claimed in claim 17, wherein the pharmaceutical composition is administered at a daily dose of from about 5 mg to about 1000 mg.

20. A method of neuroprotection in a patient in need of such protection, comprising administering to the patient a neuroprotecting effective amount of a pharmaceutical composition as claimed in claim 6.

21. A method as claimed in claim 20, wherein the pharmaceutical composition is administered at a daily dose of from about 1 mg to about 5000 mg.

22. A method as claimed in claim 20, wherein the pharmaceutical composition is administered at a daily dose of from about 5 mg to about 1000 mg.

23. A method of protecting against stroke in a patient in need of such protection, comprising administering to the patient a stroke-protecting effective amount of a pharmaceutical composition as claimed in claim 6.

24. A method as claimed in claim 23, wherein the pharmaceutical composition is administered at a daily dose of from about 1 mg to about 5000 mg.

25. A method as claimed in claim 23, wherein the pharmaceutical composition is administered at a daily dose of from about 5 mg to about 1000 mg.

26. A method of treating seizures in a patient in need of such treatment, comprising administering to the patient a seizure-treating effective amount of a compound as claimed in claim 1.

27. A method of treating a neurological disorder in a patient in need of such treatment, comprising administering to the patient a neurological-disorder-treating effective amount of a compound as claimed in claim 1.

28. A method of treating epilepsy in a patient in need of such treatment, comprising administering to the patient a epilepsy-treating effective amount of a compound as claimed in claim 1.

29. A method of neuroprotection in a patient in need of such protection, comprising administering to the patient a neuroprotecting effective amount of a compound as claimed in claim 1.

30. A method of protecting against stroke in a patient in need of such protection, comprising administering to the patient a stroke-protecting effective amount of a compound as claimed in claim 1.

31. A process for preparing a compound as claimed in claim 1, comprising reducing a compound of formula III

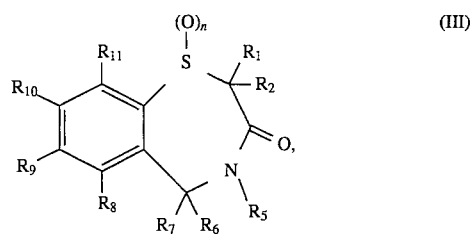

wherein n is 0, 1 or 2;

$R_1$, $R_2$, $R_6$ and $R_7$ are all H;

$R_5$ is H;

$R_8$ is selected from the group consisting of H, methyl, fluoro and chloro; and $R_9$, $R_{10}$ and $R_{11}$ are each H, a stereoisomer thereof or a pharmaceutically acceptable salt thereof, with a reducing agent to produce as a product a compound as claimed in claim 1 wherein $R_3$ and $R_4$ are each H.

32. A process as claimed in claim 31, further comprising acylating the product with an acid chloride, acid anhydride or acid to produce a compound as claimed in claim 1 wherein $R_3$ and $R_4$ are each H, and wherein $R_5$ is a group of formula —$COR_{13}$ wherein $R_{13}$ is selected from the group consisting of H, an alkyl of 1 or 2 carbon atoms and phenyl.

* * * * *

UNITED STATES PATENT AND TRADEMARK OFFICE
CERTIFICATE OF CORRECTION

PATENT NO.   : 5,580,866

DATED        : Dec. 3, 1996

INVENTOR(S)  : John R. Housley et al

It is certified that error appears in the above-identified patent and that said Letters Patent is hereby corrected as shown below:

| | |
|---|---|
| Column 21, line 30 | Insert "H, methyl," after "of". |
| Column 21, line 59 | Insert "1-" before "oxide". |
| Column 23, line 43 | Insert "H, methyl," after "of". |
| Column 23, line 65 | Insert "H, methyl," after "of". |

Signed and Sealed this

Fourth Day of November, 1997

Attest:

Attesting Officer

BRUCE LEHMAN

Commissioner of Patents and Trademarks